United States Patent
Cho et al.

(10) Patent No.: US 11,585,739 B2
(45) Date of Patent: Feb. 21, 2023

(54) METHOD FOR EXTRACTING NUCLEIC ACID USING CARTRIDGE

(71) Applicant: SD BIOSENSOR, INC., Suwon-si (KR)

(72) Inventors: Young Shik Cho, Yongin-si (KR); Hyo Guen Lee, Suwon-si (KR); Hae Joon Park, Seongnam-si (KR); Sun Young Lee, Suwon-si (KR); Kwan Hun Lim, Suwon-si (KR); In Ae Kim, Gwangmyeong-si (KR); Jae Young Kim, Suwon-si (KR); Hyo Lim Park, Suwon-si (KR); Dong Hun Kim, Suwon-si (KR)

(73) Assignee: SD BIOSENSOR, INC., Suwon (KR)

( * ) Notice: Subject to any disclaimer, the term of this patent is extended or adjusted under 35 U.S.C. 154(b) by 351 days.

(21) Appl. No.: 16/956,589

(22) PCT Filed: Dec. 20, 2018

(86) PCT No.: PCT/KR2018/016309
§ 371 (c)(1),
(2) Date: Jun. 20, 2020

(87) PCT Pub. No.: WO2019/132406
PCT Pub. Date: Jul. 4, 2019

(65) Prior Publication Data
US 2021/0285855 A1    Sep. 16, 2021

(30) Foreign Application Priority Data

Dec. 28, 2017 (KR) .................... 10-2017-0182631

(51) Int. Cl.
*G01N 1/40* (2006.01)
*G01N 1/34* (2006.01)
(Continued)

(52) U.S. Cl.
CPC ............ *G01N 1/4044* (2013.01); *G01N 1/34* (2013.01); *G01N 35/026* (2013.01); *G01N 35/08* (2013.01);
(Continued)

(58) Field of Classification Search
None
See application file for complete search history.

(56) References Cited

U.S. PATENT DOCUMENTS

| | | | |
|---|---|---|---|
| 2003/0162304 A1* | 8/2003 | Dority | B01L 3/502 436/164 |
| 2015/0209789 A1* | 7/2015 | Kho | B01L 3/523 435/287.2 |
| 2018/0087097 A1* | 3/2018 | Toumazou | C12Q 1/6825 |

FOREIGN PATENT DOCUMENTS

| KR | 10-2014-0046941 | 4/2014 |
|---|---|---|
| KR | 10-1642434 | 7/2016 |

* cited by examiner

*Primary Examiner* — P. Kathryn Wright
(74) *Attorney, Agent, or Firm* — Harvest IP Law LLP

(57) ABSTRACT

There is provided a nucleic acid extraction method using a cartridge comprising: (a) a driving part of a nucleic acid extraction device is connected to a control rod module disposed in an inner space of the upper body of a piston and a rotation control module coupled to the lower body of the piston; (b) driving the rotation control module and the control rod module, sequentially sucking sample and reagents from the plurality of chambers separated from each other into an interior space, and discharging the mixture of the interior space into the chamber of the cartridge; and (c) driving the rotation control module and the control rod module to suck the reagent inside the master mix bead chamber of the cartridge into the interior space of the piston upper body and then discharge the mixed reagent to a nucleic acid amplification module.

9 Claims, 4 Drawing Sheets

(51) Int. Cl.
    *G01N 35/08*     (2006.01)
    *G01N 35/02*     (2006.01)
    *G01N 35/10*     (2006.01)
    G01N 35/00     (2006.01)
    G01N 35/04     (2006.01)

(52) U.S. Cl.
    CPC ............... *G01N 35/1009* (2013.01); *G01N 2035/00237* (2013.01); *G01N 2035/00326* (2013.01); *G01N 2035/00544* (2013.01); *G01N 2035/0429* (2013.01)

[Fig. 1]
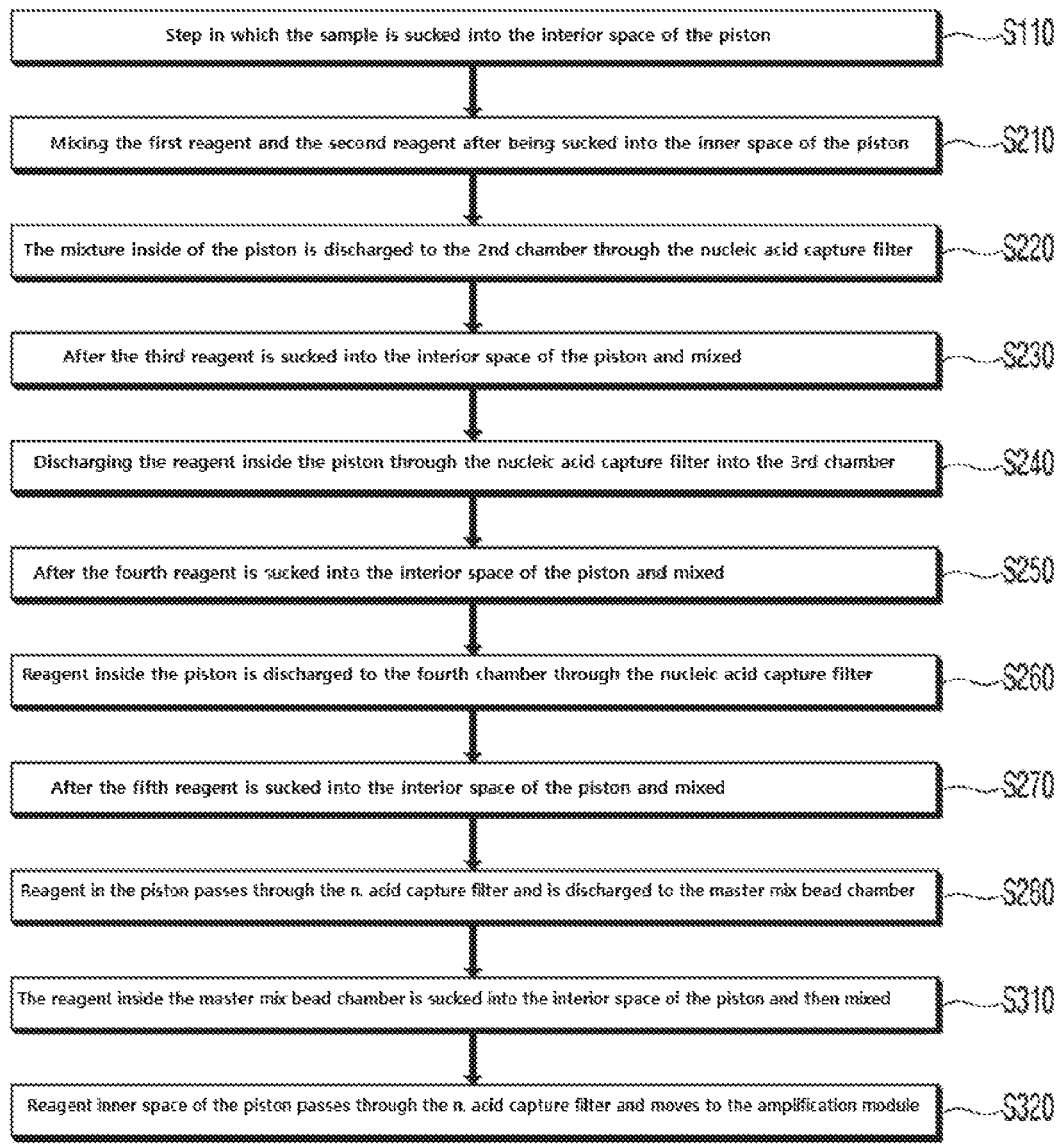

[Fig. 2]
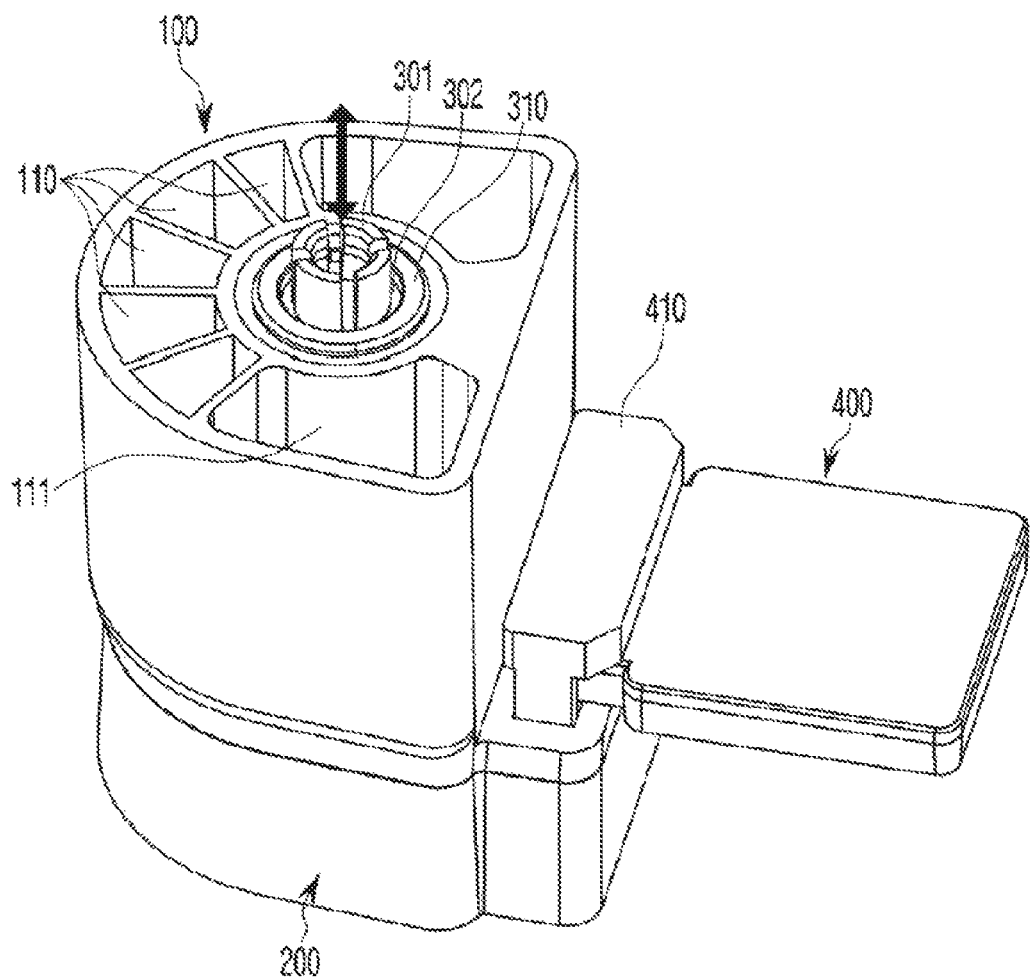

[Fig. 3]
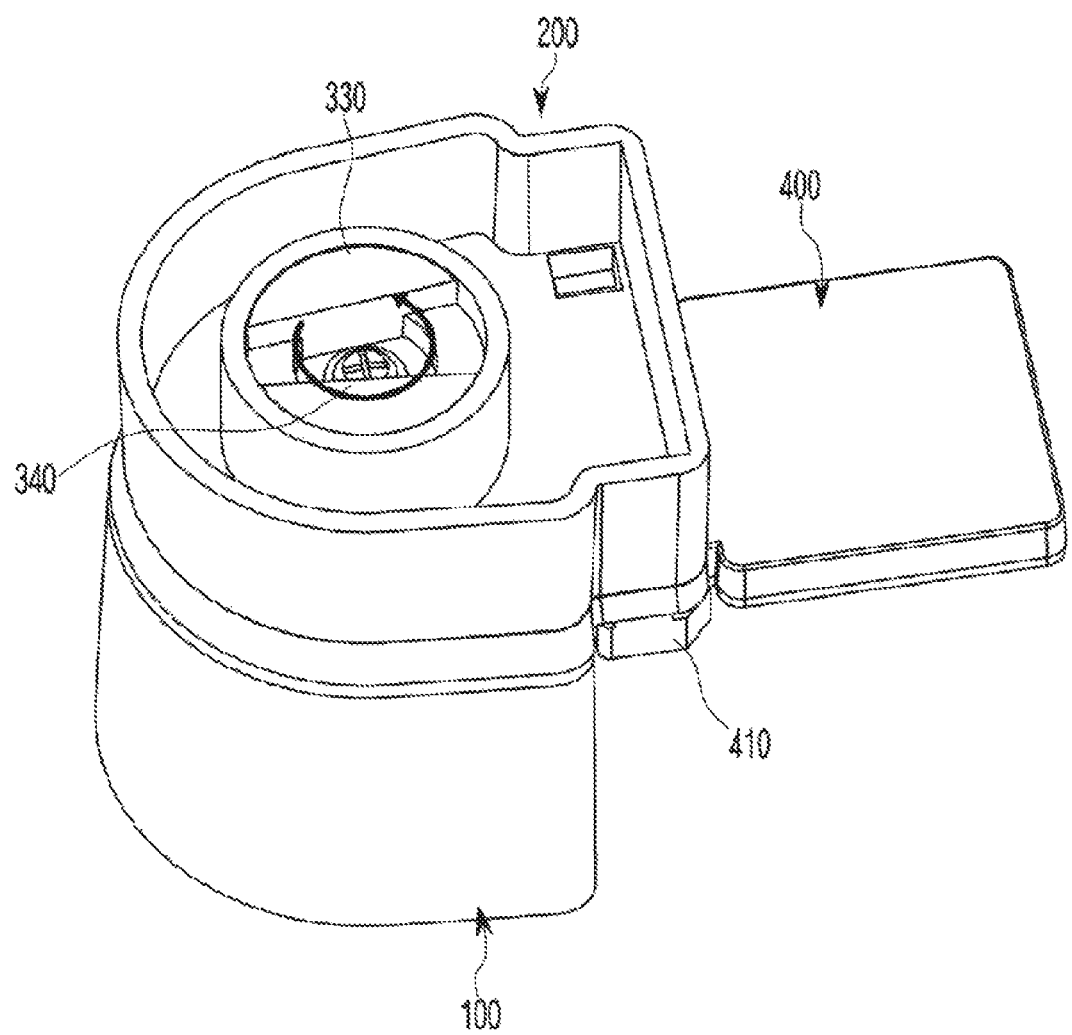

[FIG. 4]
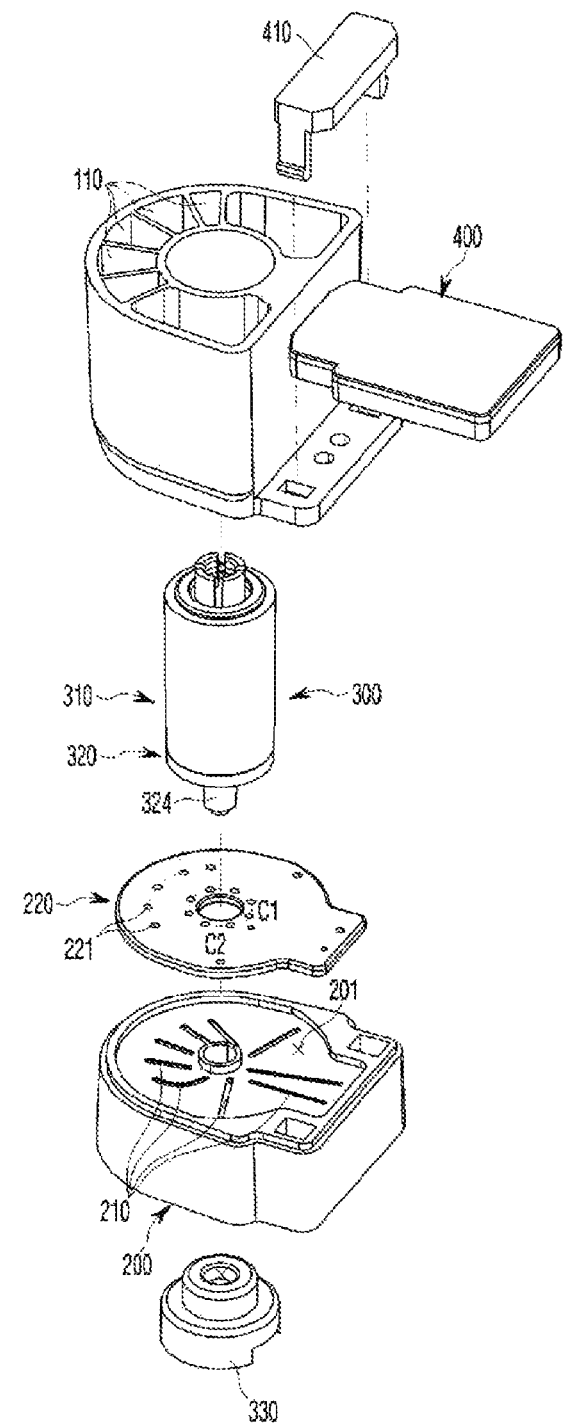

METHOD FOR EXTRACTING NUCLEIC ACID USING CARTRIDGE

TECHNICAL FIELD

The present invention relates to a nucleic acid extraction method, and more particularly, to a nucleic acid extraction method using a cartridge capable of separating and purifying nucleic acids from a sample in order to amplify the nucleic acid.

BACKGROUND ART

In modern times, it has become possible to interpret the cause of disease at the gene level with the development of biotechnology. As a result, the demand for manipulation and biochemical analysis of biological specimens to treat or prevent human diseases is increasing.

Also, in addition to the diagnosis of disease, the technology for extracting and analyzing nucleic acids from samples containing cells or biological specimens is required in various fields such as new drug development, preliminary examination of virus or bacterial infection, and forensic science.

Conventional nucleic acid extraction devices require each device for each pre-treatment process (concentration, purification), and require a long time because they must be moved to another device after one pre-treatment process. In addition, in the extraction method of the nucleic acid using the conventional nucleic acid extraction apparatus, the waste solution, which has been mixed and reacted in the extraction process, has to be discharged to a separate waste fluid chamber, and thus there is a problem that space utilization is inefficient.

Accordingly, research into a more efficient nucleic acid extraction method has been conducted to solve this problem.

DISCLOSURE

Technical Problem

The purpose of the present invention is to provide a method for extracting nucleic acids in a more efficient manner.

Technical Solution

In order to achieve the above purpose, a nucleic acid extraction method using a cartridge according to an embodiment of the present invention comprises: (a) a driving part of a nucleic acid extraction device is connected to a control rod module disposed in an inner space of the upper body of a piston and a rotation control module coupled to the lower body of the piston;

(b) driving the rotation control module and the control rod module, sequentially sucking sample and reagents from the plurality of chambers separated from each other into an interior space, and discharging the mixture of the interior space into the chamber of the cartridge; and (c) driving the rotation control module and the control rod module to suck the reagent inside the master mix bead chamber of the cartridge into the interior space of the piston upper body and then discharge the mixed reagent to a nucleic acid amplification module According to an embodiment of the present invention, the mixed solution in step (b) is discharged through a nucleic acid capture filter.

According to an embodiment of the present invention, the step (b) comprises a step of the rotation control module is driven to overlap the liquid port of the piston lower body and the sample chamber port of the cartridge, and the control rod module is driven to suck the sample in the sample chamber into the upper body interior space.

According to an embodiment of the present invention, further comprising a step of driving the rotation control module to overlap the liquid port of the piston lower body and the first reagent chamber port of the cartridge, and driving the control rod module to suck the first reagent into the interior space of the upper body, followed by mixing with the sample.

According to an embodiment of the present invention, further comprising a step of driving the rotation control module to overlap the liquid port of the piston lower body and the second reagent chamber port of the cartridge, and driving the control rod module to suck the second reagent into the interior space of the upper body, followed by mixing.

According to an embodiment of the present invention, further comprising a step of driving the rotation control module to overlap the filter port of the piston lower body and the second reagent chamber port of the cartridge, and driving the control rod module to discharge the mixed solution to the second chamber port.

According to an embodiment of the present invention, step (b) further comprises the steps of sequentially sucking, mixing, and discharging the reagents and other types of reagents.

According to one embodiment of the invention, the last sucked reagent is discharged into the master mix bead chamber of the cartridge.

According to an embodiment of the present invention, step (c) comprises the step of driving the rotation control module to overlap the filter port of the piston lower body and the master mix bead chamber port of the cartridge, and driving the control rod module to discharge the last sucked reagent into the master mix bead chamber port.

According to an embodiment of the present invention, further comprising a step of driving the rotation control module to overlap the liquid port of the piston lower body and the master mix bead chamber port of the cartridge, and driving the control rod module to suck and mix the reagent inside the master mix bead chamber into the interior space of the upper body and moving the reagent in the interior space of the piston upper body to the amplification module.

Effects of the Invention

According to a nucleic acid extraction method using a cartridge according to an embodiment of the present invention, it is possible to sequentially process a plurality of samples in a cartridge using a cartridge having a structure different from the conventional one. This makes it possible to reduce the nucleic acid extraction time and simplify the structure of the device.

In addition, according to the nucleic acid extraction method using a cartridge according to an embodiment of the present invention, it is possible to discharge the used waste liquid to the reagent chamber in the cartridge, so that the nucleic acid extraction process can be efficiently performed.

DESCRIPTION OF DRAWINGS

FIG. 1 is a flow chart of a nucleic acid extraction method according to an embodiment of the present invention.

FIG. 2 is a perspective view of a cartridge used in the present invention.

FIG. 3 is a bottom perspective view of the cartridge used in the present invention.

FIG. 4 is an exploded view of the cartridge shown in FIG. 2.

MODE FOR INVENTION

Hereinafter, the present invention will be described in more detail with reference to the drawings. In this specification, the same or similar reference numerals are assigned to the same or similar configurations in different embodiments, and the description is replaced with the first description. As used herein, a singular expression includes a plural expression unless the context clearly indicates otherwise. In addition, the suffixes "module" and "region" for components used in the following description are given or mixed only considering the ease of writing the specification, and do not have meanings or roles that are distinguished from each other.

FIG. 1 is a flowchart of a nucleic acid extraction method according to an embodiment of the present invention.

Referring to FIG. 1, the nucleic acid extraction method is a step (S110) in which the sample is sucked into the interior space of the piston, and the steps (S210 to S280) in which reagents are sucked, mixed, and discharged, and steps (S310 to S320) in which the extracted nucleic acid is move to as an amplification module.

A nucleic acid extraction method using a cartridge according to an embodiment of the present invention proceeds through the following steps.

In the step (S110) in which the sample is sucked into the interior space of the piston, the sample disposed in the chamber of the cartridge is sucked into the interior space of the piston upper body (310) by driving the piston control rod module.

A step in which the cartridge is mounted to the nucleic acid extraction device may be added, after the sample and reagents are injected into each chamber of the cartridge before the step where the sample is sucked into the inner space of the piston.

After the cartridge is mounted on the nucleic acid extraction device, the control rod module and the rotation control module are connected to a driving unit of the nucleic acid extraction device.

In the step (S210) in which the first reagent and the second reagent are sucked into the interior space of the piston and are mixed, the rotation control module rotates the piston at a certain angle to overlap the liquid port of the piston lower body with the first reagent chamber port, and the control rod module moves to the upper part of this piston and suck the first reagent. After that, the rotation control module rotates the piston at a certain angle to overlap the liquid port of the lower body of the piston with the second reagent chamber port, and when the control rod module moves to the upper portion of the piston, the second reagent is sucked.

Thereafter, the control rod module moves up and down to mix samples and reagents in the internal space.

After that, the rotation control module rotates the piston again a certain angle to overlap the filter port of the lower body of the piston with the second reagent chamber port, the control rod module moves to the lower portion of the piston, and discharges the sample and reagent mixture solution into the second reagent chamber (S220).

The filter port of the lower body of the piston is equipped with a nucleic acid capture filter to capture nucleic acid that is released when the sample and reagent mixture is discharged.

The rotation control module rotates the piston again a certain angle to overlap the liquid port of the lower body of the piston with the third reagent chamber port, and when the control rod module moves to the upper portion of the piston, the third reagent is sucked (S230).

Thereafter, the control rod module moves up and down to mix the reagents of the inner space.

The rotation control module rotates the piston again a certain angle to overlap the filter port of the lower body of the piston with the third reagent chamber port, and the control rod module moves to the lower portion of the piston to discharge the reagent to the third reagent chamber (S240).

The rotation control module rotates the piston again a certain angle to overlap the liquid port of the lower body of the piston with the fourth reagent chamber port, and sucks the fourth reagent when the control rod module moves to the upper portion of the piston (S250).

After that, the control rod module moves up and down to mix the reagents in the inner space.

The rotation control module rotates the piston again a certain angle to overlap the filter port of the lower body of the piston with the fourth reagent chamber port, and the control rod module moves to the lower portion of the piston to discharge the reagent to the fourth reagent chamber (S260).

The rotation control module rotates the piston again a certain angle to overlap the liquid port of the lower body of the piston with the fifth reagent chamber port, and sucks the fifth reagent when the control rod module moves to the upper portion of the piston (S270).

After that, the control rod module moves up and down to mix the reagents in the inner space.

The fifth reagent may be an elution reagent that elutes the nucleic acid collected in the nucleic acid capture filter.

The rotation control module rotates the piston again a certain angle to overlap the filter port of the piston lower body with the master mix bead chamber port, and the control rod module moves to the bottom of the piston and discharges the reagent to the master mix bead chamber (S280).

The fifth reagent is discharged and the nucleic acid collected in the nucleic acid capture filter is moved into the master mix bead chamber.

The rotation control module rotates the piston again a certain angle to overlap the liquid port of the piston lower body with the master mix bead chamber port, and when the control rod module moves to the upper part of the piston, the reagent inside the master mix bead chamber is sucked and the control rod module moves up and down to mix the reagent in the inner space (S310).

The rotation control module rotates the piston again a certain angle to overlap the liquid port of the lower body of the piston with the liquid port of the amplification module, the control rod module moves to the lower portion of the piston and moves the reagent to the amplification module (S320).

Hereinafter, the structure of the cartridge will be described in detail with reference to FIGS. 2 to 4.

FIG. 2 is a perspective view of the cartridge used in the present invention, FIG. 3 is a bottom perspective view of the cartridge used in the present invention, and FIG. 4 is an exploded view of the cartridge shown in FIG. 2.

For reference with FIGS. 2 to 4, the cartridge for nucleic acid extraction can largely be comprised a first body (100), a second body (200), a piston (300), a nucleic acid amplification module (400), and the like.

The first body (100) may be used for the purpose of storing a plurality of reagents.

According to the illustrated, the first body (100) may be formed of a plurality of chambers (110) forming a compartment separated from each other. Different reagents or samples are disposed in each chamber (110) and each chamber (110) forms an independent space so that the reagents do not mix with each other.

The second body (200) includes a path through which the reagent or sample stored in the first body (100) moves.

According to an embodiment of the present invention, the second body (200) may have a liquid flow path through which liquid can move and an air flow path through which air can move, and the second body (200) may include a pad (220) disposed on the upper surface to prevent leakage of liquid when combined with the first body (100). When the pad (220) and the second body (200) of cartridge are combined, the liquid flow path and the air flow path of the second body (200) are blocked by the pad (220) to form a space, thereby completing the perfect flow path (210).

The liquid flow path is connected to the first body (100) to provide a space for samples and reagents to move and mix.

The air flow path connects the amplification module and the vacuum control region of the piston (300) to control the vacuum that may occur when the extracted nucleic acid moves to the amplification module, and serves to prevent contamination of the nucleic acid amplification product.

A plurality of holes penetrating the pad (220) up and down may be formed in the pad (220). The liquid and air flow paths under the cartridge are connected to the plurality of reagent chambers (110) located in the first body (100) through the holes.

The center region of the pad (220) is coupled to be in close contact with the bottom surface of the piston lower body (320).

The holes formed in the center of the pad (220) overlap with the filter port or liquid port of the piston lower body (320) when the piston rotates.

More specifically, a plurality of flow paths (210) may be formed on the upper region of the second body (200). Each flow path (210) does not cross each other and is formed to extend from the center of the second body (200) to the outer region. As illustrated, some flow paths may have one end disposed on the same circumference and the other end also disposed on the same circumference with each other.

The pad (220) may be combined to the upper region of the second body (200).

A recessing region (201) recessed toward the bottom may be formed on the upper region of the second body (200), and the pad (220) may be engaged with the recessing region (201) on the upper region of the second body (200).

The pad (220) may seal the flow paths (210) while being in close contact with the upper surface of the second body (200). The pad (220) may be formed of rubber or synthetic resin having elasticity so that the pad (220) may be more closely adhered to the second body (200).

A plurality of holes penetrating the pad (220) up and down may be formed in the pad (220).

According to an embodiment of the present invention, the holes are arranged to overlap the top and bottom of the ends of the flow paths (210). In other words, holes formed in the pad (220) may be paired in pairs to be connected through the flow path (210).

The pad (220) may include a plurality of holes disposed on the same circumference (C1) in the center and a plurality of holes disposed on the same circumference (C2) in the outer region.

The piston (300) may be comprised of a piston upper body (310) and a piston lower body (320).

In the upper body (310) of the piston (300), an inner space where reagents and samples can be mixed is formed, and a piston (300) control rod module moving up and down may be disposed in the inner space.

The piston control rod module may include a coupling region (301) coupled with a driving unit of the nucleic acid extraction device and a closed region (302) moving up and down in close contact with the piston inner space.

The piston lower body (320) is combined with the piston upper body (310) to form one body.

The piston lower body (320) may be combined with the rotation control module (330).

According to the illustrated, the piston upper body (310) is inserted into the hole formed in the central region of the first body (100) and the shaft (324) of the piston lower body (320) is inserted into the hole formed in the central region of the second body (200).

The shaft (324) of the piston lower body (320) is fixed in engagement with the rotation control module (330) combined to the bottom of the second body (200).

The nucleic acid amplification module (400) may be combined with the first body (100) or the second body (200).

An internal flow path (210) may be formed inside the nucleic acid amplification module (400), and one end of the internal flow path may be formed to overlap with at least one of the flow paths (210) formed in the second body (200).

According to an embodiment of the present invention, there may be a fixing member (410) that covers the nucleic acid amplification module (400) and engages the first body (100) and the second body (200) so that the nucleic acid amplification module is not arbitrarily separated.

The first body (100) may include a plurality of reagent chambers (110), and each chamber (110) is formed to be isolated from each other.

At the bottom of each chamber (110), a port (121) overlapping holes formed in one end of the flow path (210) or the pad (220) is formed. Ports may have different distances from the center depending on the use of the chamber (110).

Each reagent chamber (110) comprises a single reagent chamber liquid port. Each reagent chamber liquid port is connected to the liquid flow path at the bottom of the cartridge through the liquid port connection hole of the rubber pad (220). A separate sample chamber and a master mix bead chamber (111) are combined to the sample chamber port and the master mix bead chamber port, respectively.

The sample chamber ports may be disposed on the same circumference, and the master mix bead chamber ports may be placed on different circumferences.

The sample chamber may comprise multiple dry beads required for sample extraction, and the master mix bead chamber may comprise multiple dry beads required for nucleic acid amplification.

The sample chamber and the master mix bead chamber are respectively connected to the sample chamber port and the master mix bead chamber port, and each port is connected to a hole formed in the pad and a flow path of the cartridge second body (200) to form a structure in which the liquid can move.

According to the nucleic acid extraction method using the cartridge described above, it is possible to sequentially process a plurality of samples in a cartridge using a cartridge having a structure different from the conventional one. This makes it possible to reduce the nucleic acid extraction time and simplify the structure of the device.

In addition, according to the nucleic acid extraction method using a cartridge according to an embodiment of the present invention, it is possible to discharge the used waste liquid to the reagent chamber in the cartridge, so that the nucleic acid extraction process can be efficiently performed.

The cartridge for nucleic acid extraction described above is not limited to the configuration and method of the above-described embodiments, but the above embodiments may be configured by selectively combining all or part of each embodiment so that various modifications can be made.

The invention claimed is:

1. A nucleic acid extraction method using a cartridge comprising:
  (a) providing a cartridge comprising:
    a first body including a hole formed in a central portion of a first body, a plurality of chambers and a master mix bead chamber formed around a hole in the central portion and separated from each other;
    a second body coupled to a lower portion of the first body:
    a piston disposed in the hole formed in the central portion to suck or discharge reagents in each chamber and to mix the reagent in the inner space;
    a plurality of substantially straight flow paths formed on the upper portion of the second body to extend from the center portion to the outer portion of the second body; and
    a pad disposed between the first body and the second body to cover the plurality of flow paths and having holes on a first circumference (C1) disposed to overlap one end of the plurality of flow paths and a lower surface of the piston, and having holes on a second circumference (C2) disposed to overlap the other end of the plurality of flow paths and each chamber; and
    wherein the piston comprises:
      an upper body disposed in the hole formed in the central portion of the first body and including the inner space for sucking and mixing reagents in each chamber;
      a lower body coupled to lower end of the upper body to cover lower end of the inner space and communicating with one of the holes on the first circumference (C1) of the pad during rotation;
      the piston control rod module coupled to the upper body and to cover the upper end of the inner space and is in close contact with the inner space and move up and down along the inner space; and
      a rotation control module coupled to a shaft of the lower body to rotate the lower body;
    a nucleic acid extraction device comprising a driving part connected to the piston control rod module and the rotation control module, the piston control rod module being disposed in the inner space of the upper body of the piston and the rotation control module being coupled to the lower body of the piston;
  (b) driving the rotation control module and the piston control rod module, sequentially sucking sample and reagents from the plurality of chambers separated from each other into inner space, and discharging the mixture of the inner space into one of the chamber of the plurality of chambers and a master mix bead chamber of the cartridge; and
  (c) driving the rotation control module and the piston control rod module to suck the reagent inside the master mix bead chamber of the cartridge into the inner space of the upper body and then discharge the mixed reagent to a nucleic acid amplification module.

2. The nucleic acid extraction method using a cartridge according to claim 1, wherein the step (b) comprises a step of driving the rotation control module to overlap the inner space with the sample chamber of the plurality of chambers, and driving the piston control rod module to suck the sample in the sample chamber into the inner space.

3. The nucleic acid extraction method using a cartridge according to claim 2, further comprising a step of driving the rotation control module to overlap the inner space with a first reagent chamber of the plurality of chambers, and driving the piston control rod module to suck a first reagent into the inner space, followed by mixing with the sample.

4. The nucleic acid extraction method using a cartridge according to claim 3, further comprising a step of driving the rotation control module to overlap the inner space with a second reagent chamber of the plurality of chambers, and driving the piston control rod module to suck a second reagent into the inner space, followed by mixing.

5. The nucleic acid extraction method using a cartridge according to claim 4, further comprising a step of driving the rotation control module to overlap the inner space with the second reagent chamber, and driving the piston control rod module to discharge a mixed solution to the second reagent chamber.

6. The nucleic acid extraction method using a cartridge according to claim 5, wherein the step (b) further comprises sequentially sucking, mixing, and discharging the first and second reagents and reagents different from the first and second reagents.

7. The nucleic acid extraction method using a cartridge according to claim 6, wherein the last sucked reagent is discharged into the master mix bead chamber of the cartridge.

8. The nucleic acid extraction method using a cartridge according to claim 7, wherein step (c) comprises driving the rotation control module to overlap the inner space with the master mix bead chamber of the cartridge, and driving the piston control rod module to discharge the last sucked reagent into the master mix bead chamber.

9. The nucleic acid extraction method using a cartridge according to claim 8, further comprising:
  driving the rotation control module to overlap inner space with the master mix bead chamber of the cartridge;
  driving the piston control rod module to suck and then mix the reagent inside the master mix bead chamber into the inner space; and
  moving the reagent in the inner space to the amplification module.

* * * * *